US008888746B2

(12) United States Patent
Richard et al.

(10) Patent No.: US 8,888,746 B2
(45) Date of Patent: *Nov. 18, 2014

(54) SINGLE PORT DEVICE WITH MULTI-LUMEN CAP

(71) Applicant: Covidien LP, Mansfield, MA (US)

(72) Inventors: Paul D. Richard, Shelton, CT (US); Gene A. Stellon, Burlington, CT (US); Sally Carter, Wallingford, CT (US); Brian Rockrohr, Waterbury, CT (US); Elias Hartoumbekis, New Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/786,527

(22) Filed: Mar. 6, 2013

(65) Prior Publication Data

US 2013/0184646 A1  Jul. 18, 2013

Related U.S. Application Data

(60) Continuation of application No. 13/313,301, filed on Dec. 7, 2011, now Pat. No. 8,414,485, which is a division of application No. 12/348,466, filed on Jan. 5, 2009, now Pat. No. 8,092,430.

(60) Provisional application No. 61/033,083, filed on Mar. 3, 2008.

(51) Int. Cl.
  *A61M 5/178* (2006.01)
  *A61B 17/34* (2006.01)
  *A61B 17/00* (2006.01)

(52) U.S. Cl.
  CPC ......... *A61B 17/3498* (2013.01); *A61B 17/3421* (2013.01); *A61B 17/3423* (2013.01); *A61B 17/3462* (2013.01); *A61B 17/3474* (2013.01); *A61B 2017/3445* (2013.01); *A61B 2017/3449* (2013.01); *A61B 2017/3466* (2013.01); *A61B 2017/3486* (2013.01); *A61B 2017/00477* (2013.01)
  USPC ................................. 604/167.01; 604/167.03

(58) Field of Classification Search
  CPC ........... A61B 17/3421; A61B 17/3423; A61B 17/3462; A61B 17/3474; A61B 17/3498; A61B 2017/00477; A61B 2017/3445; A61B 2017/3449; A61B 2017/3466; A61B 2017/3486
  USPC .......................... 604/167.01–167.06, 167.03; 600/207–208; 606/108
  See application file for complete search history.

(56) References Cited

U.S. PATENT DOCUMENTS 2,493,326 A    1/1950 Trinder
(Continued)

FOREIGN PATENT DOCUMENTS

DE    1893771    5/1964
EP    0550069    7/1993
(Continued)

OTHER PUBLICATIONS

European Search Report for corresponding EP09250324 date of mailing is Jul. 25, 2011 (3 pages).

(Continued)

*Primary Examiner* — Theodore Stigell

(57) ABSTRACT

A surgical access apparatus includes an access member defining a longitudinal axis and having a longitudinal passageway for reception and passage of a surgical object and an access housing mountable to the access member. The access housing includes a diaphragm mounted thereto. The diaphragm is adapted for rotational movement about the longitudinal axis relative to the access housing. The diaphragm defines at least one internal pocket and has a seal assembly disposed within the internal pocket. The seal assembly has an interface seal member adapted for establishing a fluid tight seal about the surgical object. The seal assembly is adapted for selective movement within the pocket about multiple axes in response to manipulation of the surgical object.

14 Claims, 6 Drawing Sheets

(56) References Cited

U.S. PATENT DOCUMENTS

| | | | |
|---|---|---|---|
| 5,209,737 | A | 5/1993 | Ritchart et al. |
| 5,211,370 | A | 5/1993 | Powers |
| 5,211,633 | A | 5/1993 | Stouder, Jr. |
| 5,342,315 | A | 8/1994 | Rowe et al. |
| 5,350,362 | A * | 9/1994 | Stouder, Jr. .............. 604/167.03 |
| 5,375,588 | A * | 12/1994 | Yoon ............................ 600/114 |
| 5,385,553 | A | 1/1995 | Hart et al. |
| 5,389,080 | A | 2/1995 | Yoon |
| 5,395,342 | A | 3/1995 | Yoon |
| 5,423,761 | A | 6/1995 | Hein et al. |
| 5,429,609 | A | 7/1995 | Yoon |
| 5,441,486 | A | 8/1995 | Yoon |
| 5,460,616 | A | 10/1995 | Weinstein et al. |
| 5,478,318 | A | 12/1995 | Yoon |
| 5,512,053 | A | 4/1996 | Pearson et al. |
| 5,531,758 | A | 7/1996 | Uschold et al. |
| 5,584,847 | A | 12/1996 | Duluco et al. |
| 5,676,657 | A | 10/1997 | Yoon |
| 5,779,697 | A | 7/1998 | Glowa et al. |
| 5,792,113 | A | 8/1998 | Kramer et al. |
| 5,820,600 | A | 10/1998 | Carlson et al. |
| RE36,702 | E | 5/2000 | Green et al. |
| 6,077,288 | A | 6/2000 | Shimomura et al. |
| 6,083,203 | A | 7/2000 | Yoon |
| 6,086,603 | A | 7/2000 | Termin et al. |
| 6,162,196 | A | 12/2000 | Hart et al. |
| 6,217,555 | B1 | 4/2001 | Hart et al. |
| 6,440,063 | B1 | 8/2002 | Beane et al. |
| 6,482,181 | B1 | 11/2002 | Racenet et al. |
| 6,551,270 | B1 * | 4/2003 | Bimbo et al. .............. 604/93.01 |
| 6,942,671 | B1 | 9/2005 | Smith |
| 8,092,430 | B2 * | 1/2012 | Richard et al. ........... 604/167.01 |
| 8,414,485 | B2 * | 4/2013 | Richard et al. ................ 600/207 |
| 2004/0066008 | A1 | 4/2004 | Smith |
| 2004/0204682 | A1 | 10/2004 | Smith |
| 2005/0021222 | A1 | 1/2005 | Minami et al. |
| 2005/0212221 | A1 | 9/2005 | Smith et al. |
| 2006/0217666 | A1 | 9/2006 | Wenchell |
| 2006/0224120 | A1 | 10/2006 | Smith et al. |

FOREIGN PATENT DOCUMENTS

| | | |
|---|---|---|
| EP | 0550069 A1 | 7/1993 |
| EP | 1707133 | 10/2006 |
| EP | 1707133 A1 | 10/2006 |
| WO | WO94/04067 | 3/1994 |
| WO | WO 94/04067 A1 | 3/1994 |
| WO | WO97/42991 | 5/1997 |
| WO | WO98/48724 | 11/1998 |
| WO | WO 02/17800 A2 | 3/2002 |
| WO | WO 02/41795 | 5/2002 |
| WO | WO 03/094760 | 11/2003 |
| WO | WO2006/110733 | 10/2006 |
| WO | WO2008/121294 | 10/2008 |
| WO | WO2008/149332 | 12/2008 |
| WO | WO 2009/035663 A2 | 3/2009 |
| WO | WO 2009/080399 A2 | 7/2009 |

OTHER PUBLICATIONS

Japanese Office Action 2009-29173 dated Apr. 19, 2013.
Japanese Laid-Open Publication No. 2002-28163.
Partial European Search Report for EP 09250324.2-2310 date of completion is Sep. 16, 2010 (6 pages).

* cited by examiner

SINGLE PORT DEVICE WITH MULTI-LUMEN CAP

CROSS-REFERENCE TO RELATED APPLICATIONS

The present application is a continuation of U.S. patent application Ser. No. 13/313,301, filed on Dec. 7, 2011, which is a divisional of U.S. patent application Ser. No. 12/348,466, filed Jan. 5, 2009, now U.S. Pat. No. 8,092,430, which claims the benefit of, and priority to, U.S. Provisional Patent Application Ser. No. 61/033,083, filed Mar. 3, 2008, now expired. The entire content of each of the applications identified above is incorporated by reference herein.

BACKGROUND

1. Technical Field

The present disclosure relates to a seal system adapted to permit the introduction of surgical instrumentation into a patient's body. In particular, the present disclosure relates to a seal system for use with an introducer or access device which is intended for insertion into a patient's body, and to receive one or more instruments in sealing engagement therewith.

2. Description of the Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere. In view of the need to maintain the atmospheric integrity of the inner area of the cavity, a seal assembly for a cannula, which permits introduction of a wide range of surgical instrumentation and maintains the atmospheric integrity of the inner area of the cavity, is desirable. In this regard, there have been a number of attempts in the prior art to achieve such sealing requirements. A difficulty encountered with conventional seal assemblies, however, is the inability of surgical systems to accommodate more than one instrument simultaneously into the operating cavity or the ability to repeatedly interchange between two or three instruments during a given surgical procedure without removing the instrument from the seal housing. The overall manipulation of instrumentation into and out of the seal housing and cannula in these instances often present difficulties with respect to maintaining seal integrity over repeated use and long surgical procedures.

SUMMARY

Accordingly, the present disclosure is directed to a surgical access apparatus. The apparatus includes an access member defining a longitudinal axis and having a longitudinal passageway for reception and passage of a surgical object and an access housing mountable to the access member. The access housing includes a diaphragm mounted thereto, and adapted for rotational movement about the longitudinal axis relative to the access housing. The diaphragm defines at least one internal pocket and has a seal assembly disposed within the internal pocket. The seal assembly has an interface seal member adapted for establishing a fluid tight seal about the surgical object. The seal assembly is adapted for selective movement within the pocket about multiple axes in response to manipulation of the surgical object. The diaphragm may include a plurality of pockets. Each pocket has a seal assembly and associated interface seal member disposed therein. Each seal assembly may include a zero closure valve adapted to open to permit passage of the surgical object and close in the absence of the surgical object.

In one embodiment, each seal assembly includes a gimbal mount. The gimbal mount is adapted to cooperate with internal surfaces defining a respective pocket to permit articulation of the seal assembly. A low friction material may be associated with each pocket to facilitate rotation of a respective seal assembly. Similarly, a low friction material may be associated with the access housing to facilitate rotation of the diaphragm.

The access housing may be adapted for releasable coupling to the access member. The access member includes a sleeve dimensioned for positioning within a tract defined within tissue. The sleeve may be substantially flexible. Proximal and distal rings may be associated with the sleeve for respectively engaging tissue on opposed sides of the tissue tract. At least the distal ring is deformable to permit passage through the tissue tract. The distal ring may be selectively inflatable to expand from a non-inflated configuration to facilitate insertion of the distal ring into the operating cavity to an expanded configuration to secure the distal ring relative to the tissue. The proximal ring may be selectively inflatable to expand from a non-inflated configuration to an expanded configuration to facilitate securement of the proximal ring relative to the tissue. The flexible sleeve may be selectively inflatable and acts as a conduit for conveying expansion gases between the proximal and distal rings. The proximal ring may include at least one interface which is configured to mechanically engage and releasably secure the access housing to the access member.

Other features and advantages of the present disclosure will become apparent from the following detailed description, taken in conjunction with the accompanying drawings, which illustrate, by way of example, the principals of the present disclosure.

BRIEF DESCRIPTION OF THE DRAWINGS

The foregoing features of the present disclosure will become more readily apparent and will be better understood by referring to the following detailed description of preferred embodiments, which are described hereinbelow with reference to the drawings wherein.

DETAILED DESCRIPTION

The seal assembly of the present disclosure, either alone or in combination with a seal system internal to a cannula assembly, provides a substantial seal between a body cavity of a patient and the outside atmosphere before, during and after insertion of an instrument through the cannula assembly. Moreover, the seal assembly of the present disclosure is capable of accommodating instruments of varying diameters by providing and maintaining a gas tight seal with each instrument when inserted and manipulated. The flexibility of the present seal assembly greatly facilitates endoscopic surgery where a variety of instruments having differing uses are needed simultaneously or repeatedly during a given surgical procedure and it is impracticable to repeatedly withdraw and insert multiple instruments into and out of the operating cavity through one or more cannula assemblies during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the present disclosure contemplates allowing multiple instruments of varying use to be inserted through a single cannula assembly and utilized either simultaneously or interchangeably (i.e., rotated in and out of use by the surgeon) while maintaining seal integrity and minimizing the entry and exit of gases and/or fluids to/from the body cavity. Examples of instrumentation which may be utilized for this purpose include: clip appliers, graspers, dissectors, retractors, staplers, laser probes, photographic devices, endoscopes and laparoscopes, tubes, and the like. Such instruments will be collectively referred to herein as "instruments or instrumentation".

In the following description, as is traditional the term "proximal" refers to the portion of the instrument or assembly closest to the operator while the term "distal" refers to the portion of the instrument or assembly remote from the operator.

Figure 1:
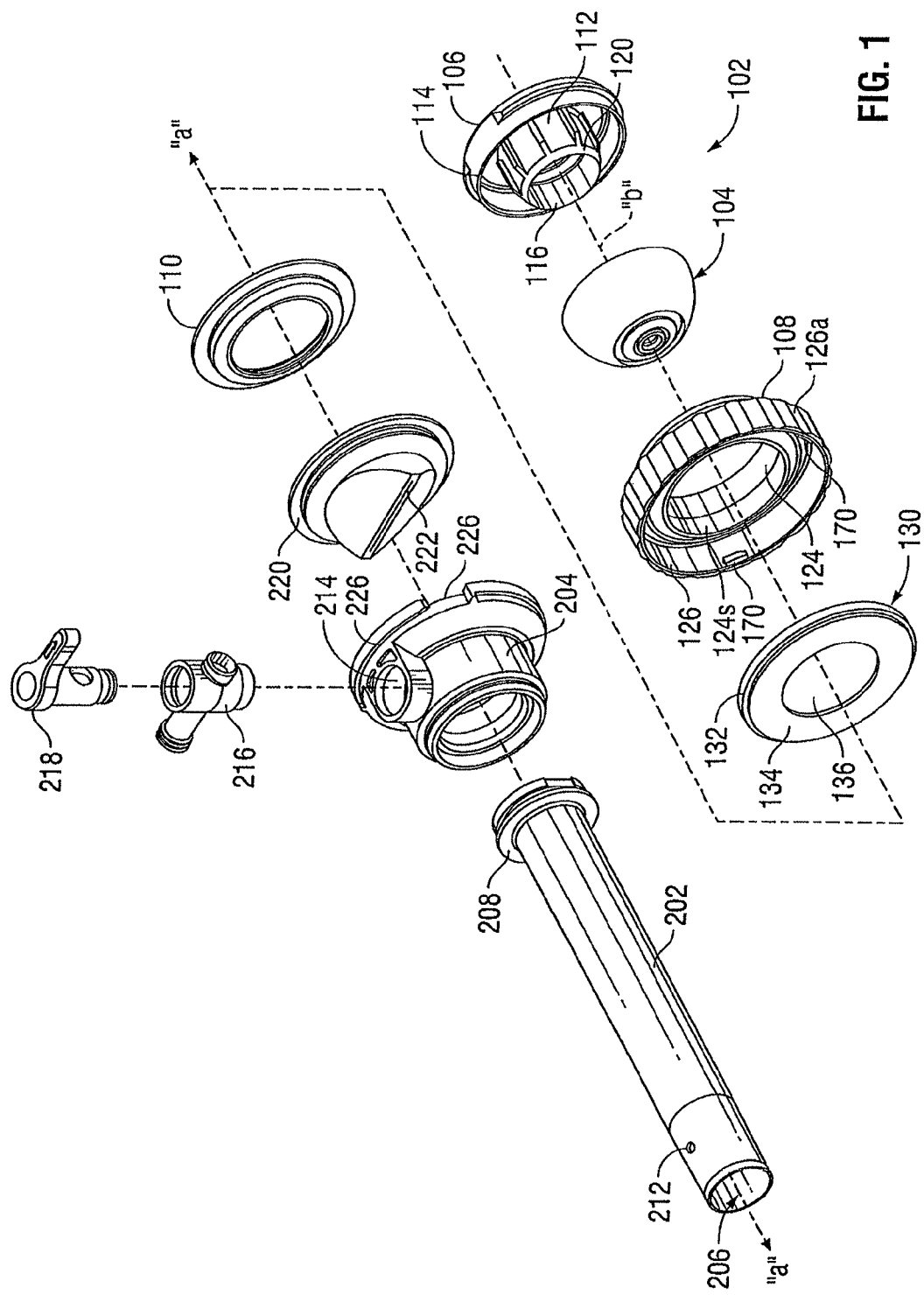
FIG. 1 is an exploded, perspective view of a cannula and seal assembly of a prior art surgical introducer system.

Referring now to the drawings, in which like reference numerals identify identical or substantially similar parts throughout the several views, FIG. 1 illustrates a known prior art seal assembly 100 mounted to a common type of cannula assembly 200. For the purposes herein, only the basic operating features of these assemblies 100 and 200 are described by way of example, and it is envisioned that any number of different types of seal assemblies and cannula assemblies may be utilized with the present disclosure without defeating the novel aspects of the same.

Cannula assembly 200 may be any conventional cannula suitable for the intended purpose of accessing a body cavity and permit introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator or trocar assembly (not shown) which is a sharp pointed instrument positionable within the passageway of the cannula assembly 200. The obturator assembly is utilized to penetrate the abdominal wall and then subsequently removed from the cannula assembly 200 to permit introduction of the surgical instrumentation utilized to perform the procedure.

With reference to FIG. 1, cannula assembly 200 includes cannula sleeve 202 and cannula housing 204 mounted to an end of the sleeve 202. The cannula sleeve 202 may be mounted to the cannula housing 204 in any known fashion including threaded arrangements, bayonet couplings, snap-fit arrangements, adhesives, etc. Cannula sleeve 202 and cannula housing 204 may also be integrally formed depending upon a particular manufacturing preference. Sleeve 202 further defines an internal longitudinal passage 206 dimensioned to permit passage of surgical instrumentation along a longitudinal axis "a" defined therethrough. Sleeve 202 defines collar 208 which is mounted to cannula housing 202 having an inner tapered wall (not shown) adjacent the collar 208 which assists in guiding the inserted instrumentation into longitudinal passage 206.

Adjacent the distal end of cannula sleeve 202 is an aperture 212 defined therein which extends through the wall of the sleeve 202 and which permits passage of insufflation gases through cannula sleeve 202 during the surgical procedure. Sleeve 202 may be clear or opaque and may be formed of stainless steel or other rigid materials such as a polymeric material or the like.

Cannula housing 204 includes port opening 214 having luer-type fitting 216 defined therein positioned within the port opening 214. Luer fitting 216 is adapted for connection to a supply of insufflation gases as is conventional in the art and incorporates valve 218 to selectively open and close the passage of the luer fitting 216. Cannula housing 204 further includes duckbill or zero closure valve 220 which tapers distally and inwardly to a sealed configuration. Closure valve 220 defines slit 222 which opens to permit passage of the surgical instrumentation and closes in the absence of the instrumentation. Closure valve 220 is typically adapted to close upon exposure to the forces exerted by the insufflation gases in the internal cavity. Other zero closure valves are also contemplated including single or multiple slit valve arrangements, trumpet valves, flapper valves, etc. Cannula housing 204 includes at least one locking recess 226 (and typically two recesses arranged in diametrically opposed relation). Locking recesses 226 serve to releasably secure seal assembly 100 to cannula assembly 200.

With continued reference to FIG. 1, seal assembly 100 is typically adapted for releasable connection to the cannula assembly 200. Alternatively, seal assembly 100 may be incorporated as part of cannula assembly 200. Seal assembly 100 includes a seal housing, generally identified as reference numeral 102, and gimbal mount 104 which is disposed within the seal housing 102. For the purposes herein, a so-called "gimbal" or "gimbal mount" is a mechanical device that allows the rotation of an object in multiple dimensions or along multiple axes.

Seal housing 102 houses the sealing components of the assembly and defines the outer valve or seal body of the seal assembly 100. Seal housing 102 defines central seal housing axis "b" which is typically parallel to the axis "a" of cannula sleeve 202 and, more specifically, coincident with the axis "a" of the cannula sleeve 202. Seal housing 102 incorporates three housing components, namely, first, second and third housing components 106, 108, 110, respectively, which, when assembled together, form the seal housing 102. Assembly of housing components 106, 108, 110 may be affected by any of the aforementioned connection means discussed with respect to cannula housing 204.

First housing component 106 defines inner guide wall 112 and outer wall 114 disposed radially outwardly of the inner guide wall 112. Inner guide wall 112 defines central passage 116 which is dimensioned to receive a surgical instrument and laterally confine the instrument within seal housing 102. Inner guide wall 112 is generally cylindrical in configuration and terminates in a distal arcuate or rounded surface 120.

Second housing component 108 inner cylindrical wall 124 and outer wall 126 have a transverse wall (not shown) disposed therebetween. Inner cylindrical wall 124 is dimensioned to mate with outer wall 114 of first housing component 106, i.e., in a manner to be positioned within the interior of the outer wall 114 in frictional relation therewith. In the alternative, outer wall 114 of first housing component 106 may be adhered to inner cylindrical wall 124 of second housing component 108. Outer wall 126 defines a scalloped outer surface 126a that is dimensioned for gripping engagement by the user. Extending contiguously from inner cylindrical wall 124 in the distal direction is an arcuate or cup-shaped gimbal wall support 124s which supports gimbal mount 104.

Seal assembly 100 further includes interface seal 130 mounted adjacent gimbal mount 104. Interface seal 130 functions in minimizing the loss of insufflation gases through seal assembly 100. Interface seal 130 includes interface seal mount 132 and flexible interface seal member 134 secured to the seal mount 132. Seal mount 132 is typically annular in configuration and is fabricated from a relatively rigid material such as a polymeric material or stainless steel. Interface seal member 134 may be fabricated from an elastomeric material having qualities to engage seal mount 104 in substantial sealed relation therewith. Interface seal member 134 defines central aperture 136 which receives the forward or distal surface of gimbal mount 104. Interface seal member 134 extends radially inwardly and longitudinally relative to seal housing axis "b" when assembled within seal housing 102. This configuration increases the amount of surface area of interface seal member 134 engaging the outer surface of gimbal mount 104 thereby facilitating the formation and maintenance of a seal about the gimbal mount during manipulation of the instrument. Interface seal 130 may further include a gasket seal (not shown) mounted adjacent the proximal side of interface seal mount 132 which serves to form a seal with the intermediate wall to substantially minimize passage of fluids through seal housing 102.

Figure 2:
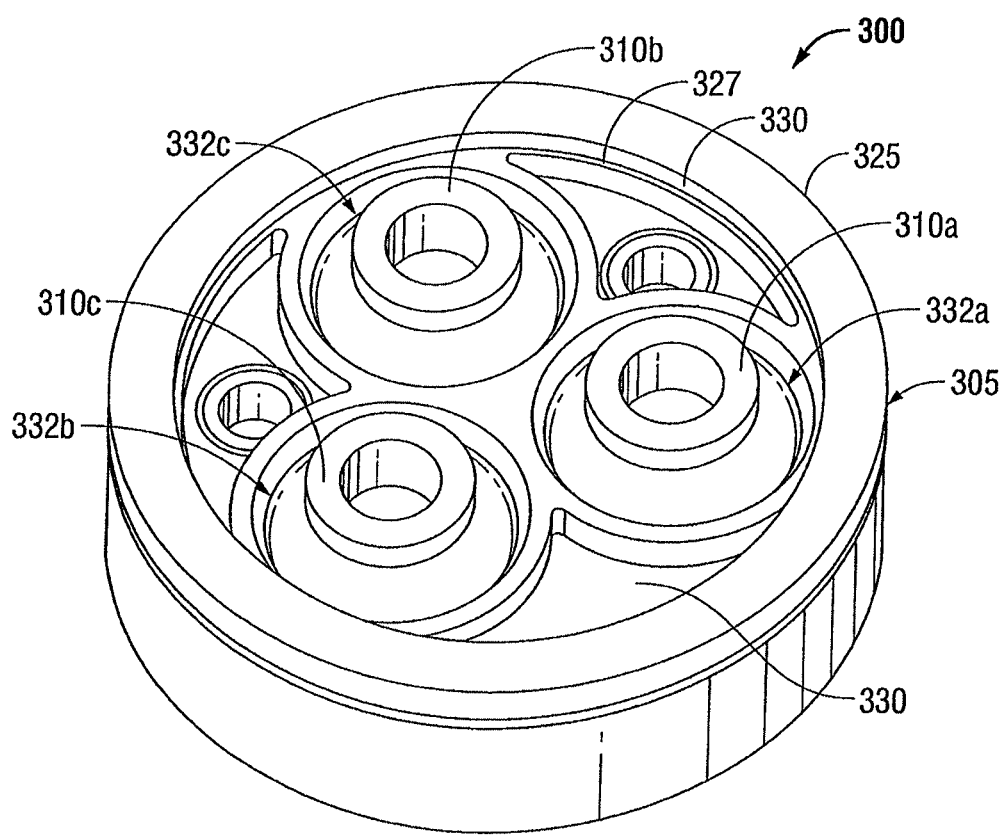
FIG. 2 is a top, perspective view of a seal assembly according to the present disclosure with multiple gimbal seals disposed therein.

FIG. 2 shows one embodiment of a multiple gimbal seal assembly 300 according to the present disclosure which includes a gimbal or seal housing 305 having an outer periphery 325 configured to selectively and releasably engage a corresponding inner peripheral surface 412 of an access member or cannula assembly 400 as described in more detail below with respect to the description of FIG. 5. Access or seal housing 305 also includes an inner periphery 327 configured to rotatingly engage a diaphragm 330 which, in turn, supports a plurality of gimbal seals 310a, 310b and 310c thereon. Diaphragm 330 is engaged for selective rotation within the inner periphery 327 of seal housing 305 and includes an outer profile 334 which is configured to mechanically engage an inner profile 360 of inner surface 327 of housing 305 such that diaphragm 330 is rotatable relative to housing 305 in the direction "R" (See FIG. 6). It is envisioned that any number of known support surfaces, bearings, friction-fit arrangements and gear assemblies known in the art may be utilized to accomplish this purpose. For the purposes herein, inner profile 360 and outer profile 334 may include inter-engaging surfaces, e.g., support 330a on diaphragm 330 and notch 361 on inner profile 360 may be configured to facilitate rotation or engagement between the two components 330 and 305. Either or both of these surfaces 330a and/or 360 may be coated with a low friction material 375 to further facilitate relative rotational movement of the diaphragm 330 with respect to the seal housing 305. Examples of low friction materials include synthetic resinous fluorine containing polymers, tapes, silicone, filaments, solutions, emulsions and polytetrafluoroethylene coatings such as one particular synthetic polymer commonly sold under the trademark TEFLON®. As can be appreciated, the user may manipulate, orient and interchange instruments within the operating cavity by rotating the diaphragm 330 relative to the seal housing 305.

Figure 3:
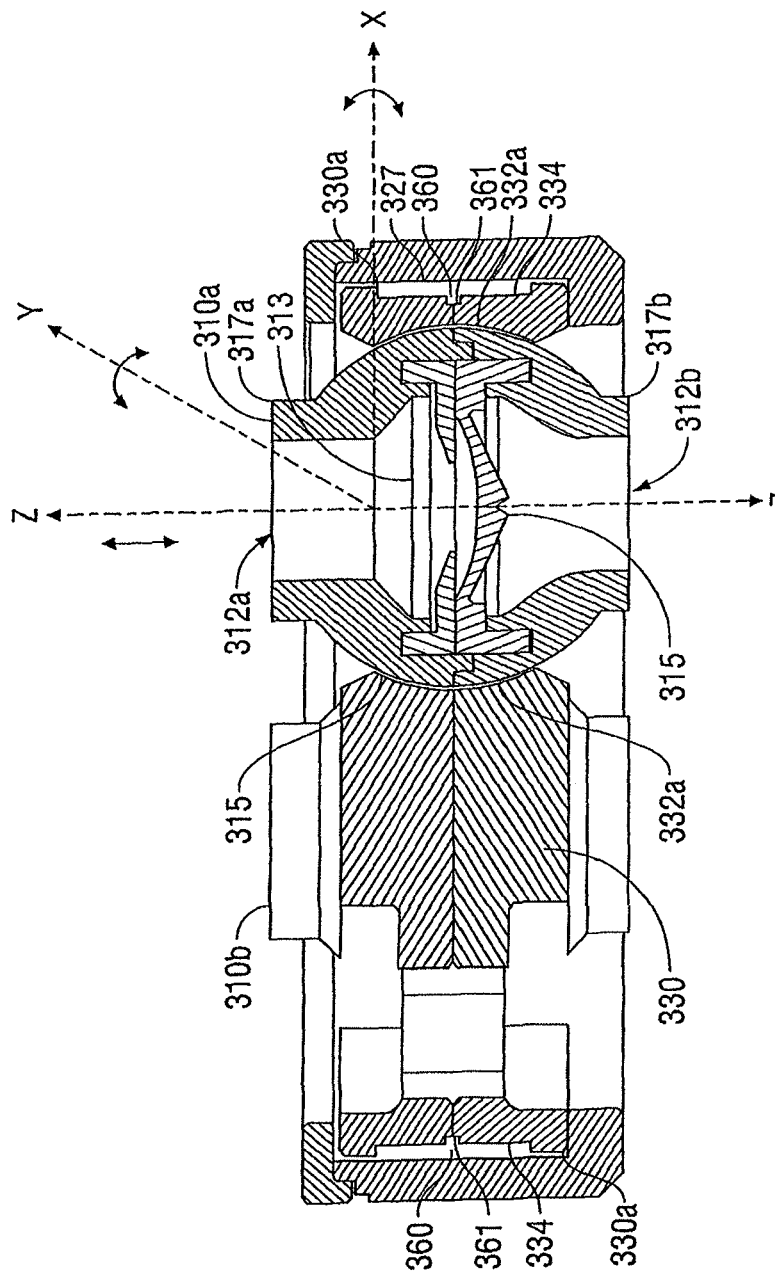
FIG. 3 is a side cross-sectional view of the seal assembly of FIG. 2.

FIG. 3 is a cross sectional detail showing the inner working details of the gimbal seal assembly 300 and, more particularly, the internal aspects of gimbal seal 310a and the rotating engagement of the inner profile 360 of housing 305 and outer profile 334 of diaphragm 330. For the purposes herein, gimbal seal 310a is shown in cross section by way of example although it should be appreciated that the other gimbal seals 310b and 310c contain similar internal operating components and have similar operating features.

Gimbal seal 310a includes a generally ball-shaped outer periphery 314 and is configured to seatingly engage a corresponding pocket 332a defined within diaphragm 330 such that the gimbal seal 310a is supported in a ball and socket manner within the seal housing 305 in friction-fit, fluid tight engagement. Gimbal seal 310a includes proximal and distal ends 311a and 311b which define corresponding proximal and distal openings 312a and 312b, respectively, within gimbal seal 310a. Proximal and distal openings 312a and 312b are configured for passage of surgical instrumentation (not shown) therethrough and may include various internal features such as an internal taper or instrument guide 313 or low friction coatings (not shown) to facilitate passage of the surgical instrumentation therethrough.

Gimbal seal 310a also includes a zero closure valve 315 disposed therein which permits passage of surgical instrumentation (not shown) therethrough and closes in the absence thereof and is configured to particularly remain closed upon exposure to the internal pressures associated with insufflation. Other types of zero closure valves are also contemplated including duck bill valves, single or multiple slit valves, trumpets valves, flapper valves, etc. As surgical instrumentation is passed through opening 312a and into gimbal seal 310a, the zero closure valve 315 opens distally permitting passage of the instrument therethrough while maintaining a fluid tight seal against the instrument at all times when the instrument is manipulated within the operating cavity.

As mentioned above, diaphragm 330 supports gimbal seal 310a in friction-fit, fluid tight engagement by virtue of the mechanical, ball and socket engagement of the outer periphery 314 of the gimbal seal 310a and the pocket cavity defined within diaphragm 330. This type of arrangement enables the user to manipulate the surgical instrument into and out of the operating cavity relative to the z-axis, and rotate the instrument relative to the x and y axes to position the instrument as desired. In other words, the ball-and-socket arrangement of the seal 310a in the pocket 332a allows the instrument and seal 310a to pivot and rotate together relative to the diaphragm 330 pocket 332a along the x and y axes (e.g., in the directions about the axes as shown in FIG. 3 and in the directions "IR1-IR3" as shown in FIG. 7).

As can be appreciated and as illustrated in the present embodiment, three gimbal seals 310a, 310b and 310c are shown disposed within the diaphragm 330 of seal housing 305. This enables a surgeon to utilize three instruments within the operating cavity at the same time without having to remove any one instrument from the operating cavity for substitution purposes. In other words, the surgeon can simultaneously utilize the three instruments (if desired) within the operating cavity or rotate each instrument (of the three) into and out of engagement with a particular area within the operating cavity by rotating the diaphragm 330 relative to the seal housing 305 (as explained above) without compromising the integrity of the pneumoperitoneum.

Figure 6:
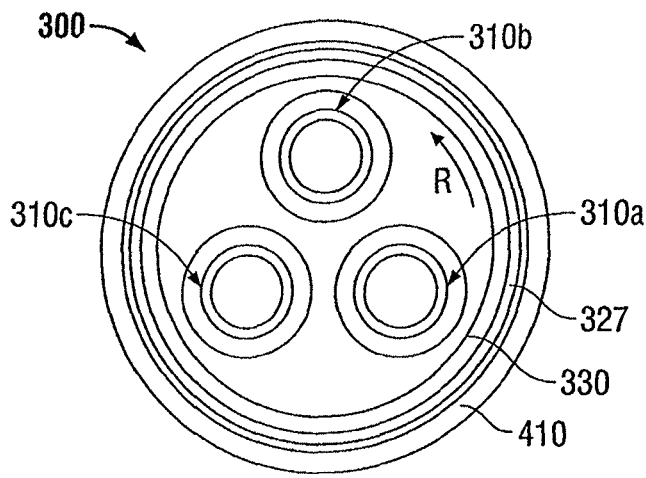
FIG. 6 is a top schematic view showing relative rotation of an inner support diaphragm relative to the seal assembly.
Figure 7:
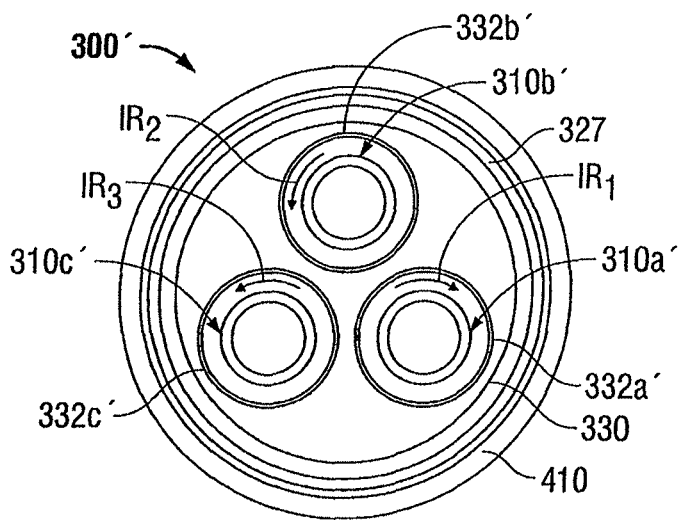
FIG. 7 is a top schematic view showing rotation of the individual gimbal seals relative to the inner support diaphragm of the seal assembly.
Figure 8:
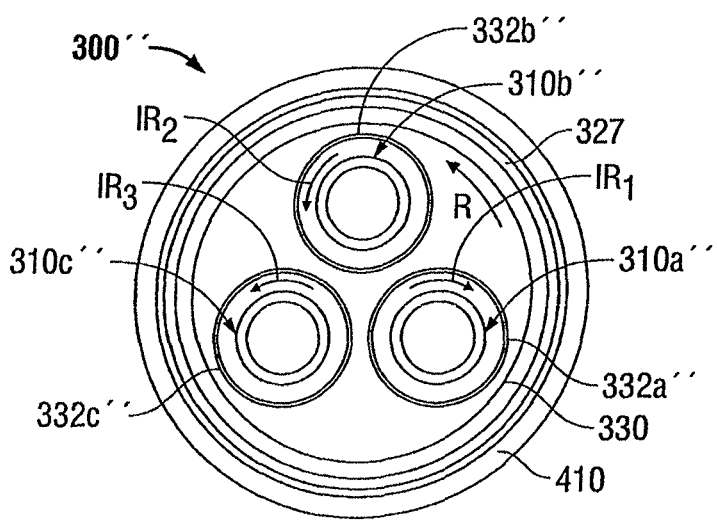
FIG. 8 is a top schematic view showing both relative rotation of an inner support diaphragm relative to the seal assembly and rotation of the individual gimbal seals relative to the inner support diaphragm of the seal assembly.

Alternatively, it is envisioned that the gimbal seal 310a and the instrument may also be rotated about or moved along the z-axis without compromising the integrity of the pneumoperitoneum (See FIGS. 7 and 8). In other words, the surgeon would not only have the ability to rotate different instruments into and out of a particular operating area within the operating cavity by rotating the diaphragm 330 relative to the seal housing 305 (See FIG. 6), but the surgeon may also have the ability to rotate the instrument (or any of the instruments either simultaneously or independently) within the pocket 332a (or other pockets 332b and 332c (See FIG. 2)) of the diaphragm 330 about the z-axis.

Figure 4:
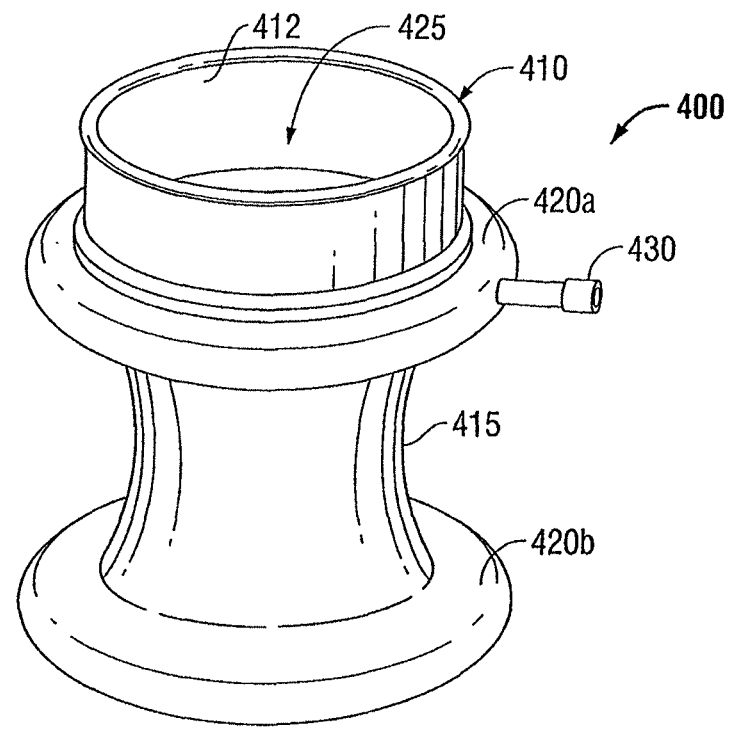
FIG. 4 is a top perspective view of a cannula assembly according to the present disclosure for use with the seal assembly of FIG. 2.

FIG. 4 shows one envisioned embodiment of a cannula assembly 400 for use with the seal assembly 300 as described above. More particularly, cannula assembly 400 includes proximal and distal support rings 420a and 420b separated by a flexible sleeve 415 disposed therebetween. Rings 420a and 420b also include a common internal chamber 421 defined therebetween which is selectively inflatable by a nozzle 430 attached to ring 420a. As explained in more detailed below with respect to the operation of the seal and cannula assemblies 300 and 400, respectively, sleeve 415 provides a passageway for chamber 421 between rings 420a and 420b such that introduction of an inflatable medium into a port 431 defined in nozzle 430 inflates both rings simultaneously (or, alternatively, sequentially depending upon a particular purpose). Once expanded or inflated, rings 420a, 420b and sleeve 415 define an elongated tubular structure having a central lumen 435 defined therethrough for selective passage of instrumentation into and out of the operating cavity.

Figure 5:
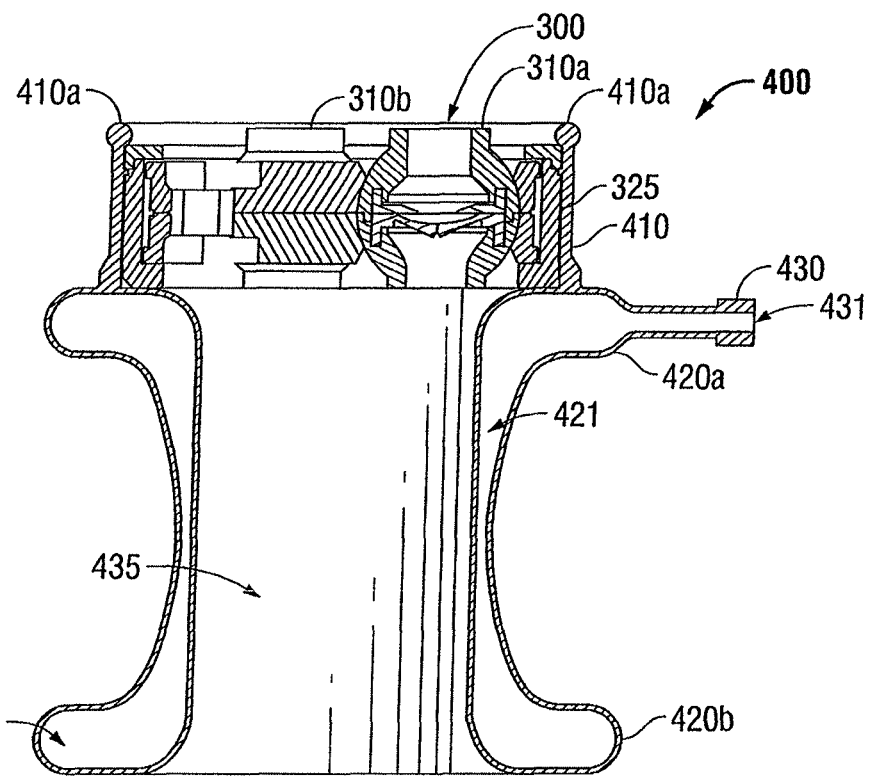
FIG. 5 is a side cross-sectional view of the cannula assembly of FIG. 4 with the seal assembly mounted therein.

As shown in FIG. 5, cannula assembly 400 also includes a seal assembly interface 410 operatively coupled to the proximal ring 420a and disposed in fluid-tight communication therewith. More particularly, seal assembly interface 410 includes an inner cavity 425 defined therein that is configured to selectively and removably receive seal assembly 300 therein. Seal assembly interface 410 includes a proximal-most edge or user-facing lip 410a which is resilient or substantially flexible to allow selective insertion and removal of seal assembly 300 in fluid-tight engagement therewith. One or more guides, tabs or other mechanical features (not shown) may be utilized to secure the seal assembly 300 within inner cavity 425.

As mentioned above, each gimbal seal, e.g., gimbal seal 310a, includes a distal opening, e.g., opening 312b, which facilitates introduction of the surgical instrumentation into the operating cavity after passage of the instrument through the zero closure valve 315. All of the distal openings of the gimbal seals (only distal opening 312b is shown in FIG. 3) are disposed in vertical registration with central lumen 435 of cannula 400 thereby enabling simultaneous introduction of multiple instruments into the operating cavity. Moreover, by vertically aligning central lumen 435 with the various distal openings of the gimbals seals 310a-310c, the surgeon can freely rotate the instruments within the lumen 435 without issue.

Figure 9:
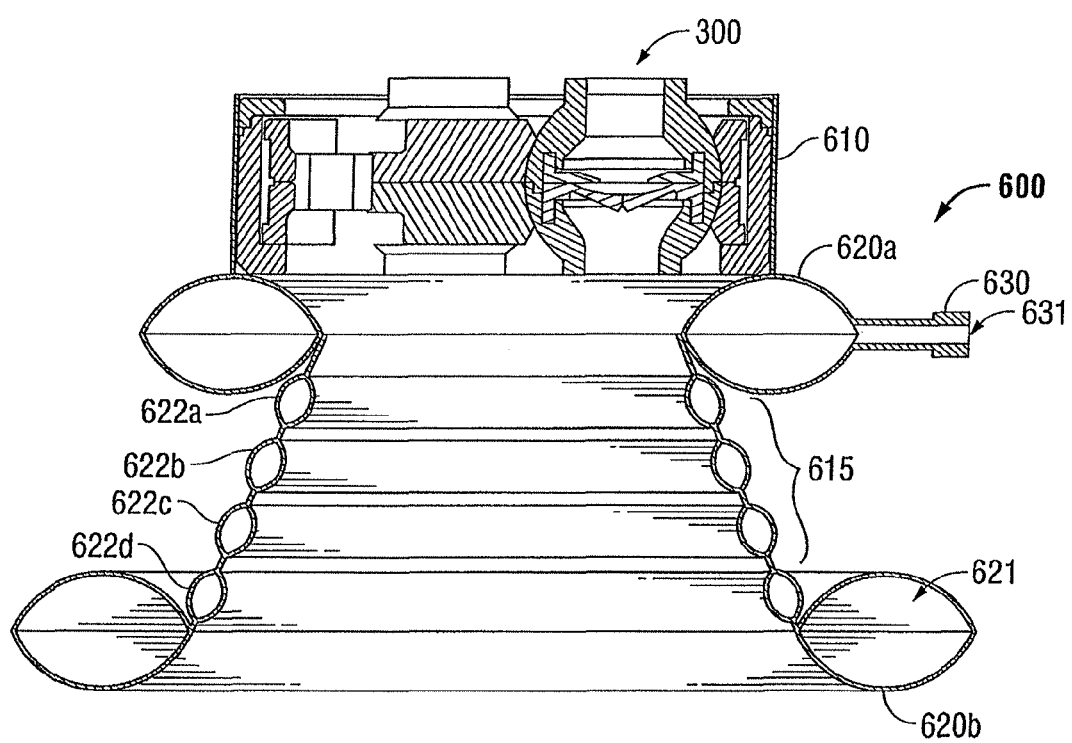
FIG. 9 is a side cross-sectional view of another embodiment of a cannula assembly having a series of inflatable concentrically-disposed rings which cooperate to secure the cannula to the inner abdominal walls of an operatively cavity.

FIG. 9 shows yet another envisioned embodiment of a cannula assembly 600 for use with the presently disclosed seal assembly 300. More particularly, cannula assembly 600 is similar to the cannula assembly 400 shown in FIGS. 4 and 5 with the exception that the flexible sleeve 615 includes a series of concentrically-disposed inflatable rings 622a-622d of varying diameter which are configured to engage and secure against the inner abdominal wall when the cannula 600 is inflated via nozzle 630. Ring 620a is configured to have a first diameter and include a seal assembly interface 610 which is substantially flexible to allow selective insertion and removal of seal assembly 300 therein in fluid-tight engagement therewith. As shown in FIG. 9, ring 620b is configured to have a second diameter greater than the diameter of ring 620a to facilitate anchoring and stabilizing the cannula assembly 600 within the operating cavity. The diameters of the concentrically-disposed rings 622a-622d generally taper in a distal direction (i.e., into the operating cavity) from about the diameter of ring 620a to about the diameter of ring 620b which also facilitates and enhances anchoring the cannula assembly 600 against the inner abdominal wall.

Nozzle port 631 communicates an inflatable medium into rings 620a and 620b and concentric rings 622a-622d and may include one or more regulators or valves (not shown) to monitor the pressure associated therewith. A second closure valve (not shown) may be included with the cannula 600 to facilitate engagement, removal and/or swap-out of the seal assembly 300 without affecting the pneumoperitoneum.

In use, a surgeon creates an incision in an abdominal wall using a known hand access surgical technique or cuts through the skin and facia and introduces the cannula assembly 400 into the incision to create a passageway therethrough. More particularly, ring 420b and the distal end of sleeve 415 are introduced into the incision and ring 420a remains outside the incision. The seal housing 300 is selectively engaged within the inner cavity 425 of the seal interface 410. Rings 420a and 420b are then inflated with an inflatable medium via nozzle 430 which expands the inner chamber 421 against the inner walls of the abdominal cavity to create a fluid tight seal. The operating cavity is then insufflated to create a pneumoperitoneum through one or more insufflation valves disposed on the cannula assembly 400 (not shown in FIGS. 2-8, See FIG. 1).

An instrument (not shown) is inserted into any one of the gimbal seals 310a-310c of the seal assembly 300, for example, gimbal seal 310a, forced through zero closure valve 315 and into central lumen 435 of cannula assembly 400 (or 600) and into the operating cavity. The zero closure valve 315 flexes distally to accommodate the instrument diameter, as necessary. Once the instrument is properly inserted within the gimbal seal 310a, the instrument may be manipulated within seal assembly 300 and cannula assembly 400 by rotating or manipulating the instrument within the pocket 332a of diaphragm 330 along the x, y or z axes (See FIGS. 3 and 7) or rotating the diaphragm 330 relative the seal housing 305 (See FIGS. 2, 6 and 8). Additional instruments can be added into the operating cavity in a similar manner through use of one or more of the other gimbal seals 310b and 310c. The arrangement of the gimbal seal 310a-310c and zero closure valves 315 allow the instruments to freely swivel, move and rotate in multiple directions and orientations while at all times maintaining the integrity of the fluid-tight engagement with the instruments.

While the invention has been particularly shown, and described with reference to the particular embodiments, it will be understood by those skilled in the art that various modifications and changes in form and detail may be made therein without departing from the scope and spirit of the present disclosure. Accordingly, modifications such as those suggested above, but not limited thereto, are to be considered within the scope of the invention.

What is claimed is:

1. A seal assembly for use with a surgical access apparatus, the seal assembly comprising:
    a housing;
    a diaphragm rotatably secured within the housing, the diaphragm including at least one pocket defining a cavity, wherein an entirety of the diaphragm is rotatably secured within the housing; and
    a seal disposed within the cavity, the seal including an inner seal member configured as a zero closure valve adapted to open to permit passage of a surgical object, and to close absent a surgical object, the seal and the cavity including corresponding arcuate surfaces configured and dimensioned for cooperative engagement to facilitate selective articulation of the seal within the pocket about a plurality of axes.

2. The seal assembly of claim 1, wherein the seal is configured and dimensioned to establish a fluid tight seal with a surgical object upon insertion.

3. The seal assembly of claim 1, wherein the at least one pocket includes a plurality of pockets, each of the plurality of pockets defining a cavity accommodating a seal, each seal and each cavity including corresponding arcuate surfaces configured and dimensioned for cooperative engagement to facilitate selective articulation of each seal about a plurality of axes.

4. The seal assembly of claim 3, wherein each seal is configured and dimensioned to establish a fluid tight seal with a surgical object upon insertion.

5. The seal assembly of claim 4, wherein each seal includes a zero closure valve adapted to open to permit passage of a surgical object, and close absent a surgical object.

6. The seal assembly of claim 1 further comprising a low friction material associated with the pocket to facilitate articulation of the seal.

7. The seal assembly of claim 1, wherein the diaphragm includes proximal and distal surfaces, the diaphragm being secured to the housing such that the proximal surface of the diaphragm is fixedly positioned along a longitudinal axis extending through a center of the housing, whereby the proximal surface of the diaphragm remains in a substantially constant axial location during use of the diaphragm.

8. The seal assembly of claim 1, wherein the diaphragm is configured to rotatably engage an inner periphery of the housing.

9. The seal assembly of claim 8, wherein the diaphragm includes an outer periphery with a first structure, and the inner periphery of the housing includes a second structure, the first and second structures having corresponding configurations to facilitate rotation of the diaphragm in relation to the housing.

10. A surgical access apparatus, comprising:
    a housing;
    an access member extending distally from the housing along a longitudinal axis; and
    a diaphragm rotatably mounted within the housing, the diaphragm including: at least one pocket defining a cavity, wherein an entirety of the diaphragm is rotatably secured within the housing;
    a seal disposed within the cavity, the seal and the cavity including corresponding arcuate surfaces configured and dimensioned for cooperative engagement to facilitate selective articulation of the seal about a plurality of axes; and
    an inner seal member configured as a zero closure valve adapted to open to permit passage of a surgical object, and close absent a surgical object.

11. The surgical access apparatus of claim 10, wherein the diaphragm rotatably engages an inner periphery of the housing.

12. The surgical access apparatus of claim 10, wherein the diaphragm has proximal and distal surfaces, the diaphragm being secured to the housing such that the proximal surface of the diaphragm is fixedly positioned along the longitudinal axis, whereby the proximal surface of the diaphragm remains in a substantially constant axial location during use of the surgical access apparatus.

13. The surgical access apparatus of claim 10, wherein the at least one pocket includes a plurality of pockets, each of the plurality of pockets defining a cavity accommodating a seal, each seal and each cavity including corresponding arcuate surfaces configured and dimensioned for cooperative engagement to facilitate selective articulation of each seal about a plurality of axes.

14. The surgical access apparatus of claim 10 further comprising a low friction material associated with the at least one pocket to facilitate articulation of the seal.

* * * * *